United States Patent [19]

Dye

[11] Patent Number: 4,804,208

[45] Date of Patent: Feb. 14, 1989

[54] MANIFOLD COUPLING ASSEMBLY

[75] Inventor: John F. Dye, Elgin, Ill.

[73] Assignee: The Kendall Company, Boston, Mass.

[21] Appl. No.: 895,554

[22] Filed: Aug. 11, 1986

[51] Int. Cl.[4] .............................................. F16L 35/00
[52] U.S. Cl. ..................................... 285/26; 285/137.1; 285/308; 285/319; 285/423; 285/914; 285/921
[58] Field of Search ...................... 285/921, 65, 70, 71, 285/72, 73, 79, 319, 26, 29, 914, 93, 137.1, 308

[56] References Cited

U.S. PATENT DOCUMENTS

| | | | |
|---|---|---|---|
| 702,662 | 6/1902 | Lyle | 285/137.1 |
| 746,628 | 12/1903 | Field et al. | 285/137.1 X |
| 3,287,031 | 11/1966 | Simmons et al. | 285/914 X |
| 3,409,858 | 11/1968 | Krehbiel . | |
| 3,417,365 | 12/1968 | Krehbiel . | |
| 3,781,041 | 12/1973 | Petzetakis | 285/423 X |
| 4,076,279 | 2/1978 | Klotz | 285/26 |
| 4,198,961 | 4/1980 | Arkans . | |
| 4,247,133 | 1/1981 | Moller | 285/73 X |
| 4,253,449 | 3/1981 | Arkans et al. . | |
| 4,462,654 | 7/1984 | Aiello | 285/423 X |
| 4,557,261 | 12/1985 | Rugheimer . | |

Primary Examiner—Dave W. Arola
Attorney, Agent, or Firm—Donald N. Halgren

[57] ABSTRACT

The present invention comprises a manifold coupling for connecting a plurality of conduits which carry pressurized fluid in a sequential manner. Each portion of the manifold coupling is a duplicate of the other portion. Each portion has locking means and alignment means to prevent the misaligned connection of the conduits. The alignment means includes a keying arrangement built into the housing walls of each portion of the coupling. A reinforcement means is configured into the walls to prevent yielding thereof, and inadvertent misalignment of the coupling portions.

2 Claims, 2 Drawing Sheets

U.S. Patent  Feb. 14, 1989  Sheet 1 of 2  4,804,208
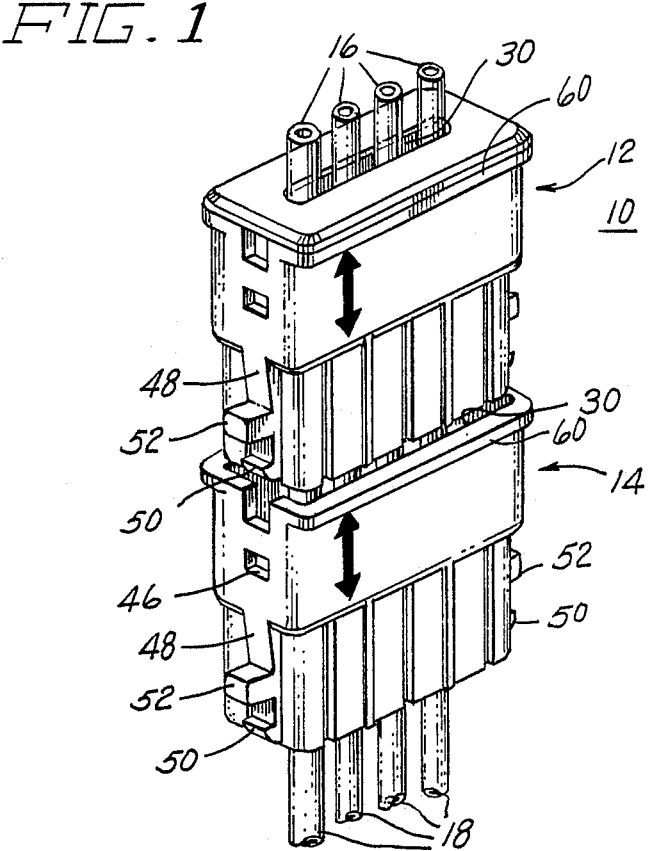
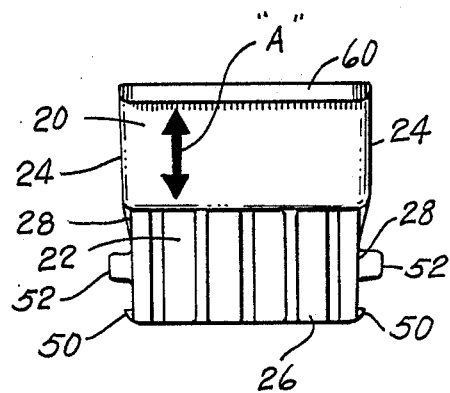
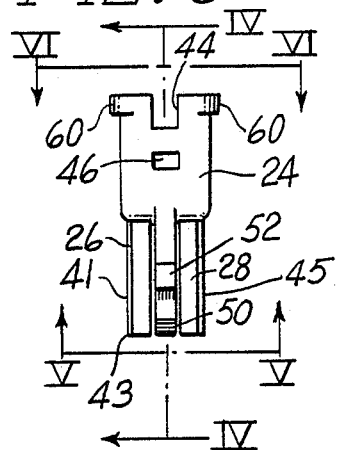

MANIFOLD COUPLING ASSEMBLY

BACKGROUND OF THE INVENTION (1) Field of the Invention

This invention relates to a connection system for fluid lines, and more particularly to an interlock and interconnection system for properly aligning a plurality of fluid lines.

(2) Prior Art

Devices for interconnecting fluid lines are varied and many. Wherever a fluid line must be connected to a second fluid line, a connection means must be arranged thereinbetween so as to prevent leakage and facilitate a quick interconnection thereof. Certain fluid machinery require a plurality of interconnected lines which must be maintained in fluid communication without leakage therefrom. Such a device is shown in U.S. Pat. No. 4,198,961. This device is a sequential compression device utilized for medical purposes wherein a series of different pressures are sequentially applied at adjacent locations on a patient's limb. The flow of compressive fluid in the pressure lines in this device is critical. Inasmuch as the pressure from one line to the other varies, the way the lines are interconnected is also critical. A device of this nature has a plurality of pressurizable chambers which are sequentially actuatable. This device is utilized during surgery or immediately thereafter to prevent the pooling or stasis of blood in a confined patient.

In any misalignment or miscommunication between respective tubing would be a serious problem. The time it would take for an interconnection to be accommodated is also of critical importance here.

U.S. Pat. No. 4,557,261 shows an interconnection system for fluid lines for use in respirators or anesthetic units. A wye piece is arranged to a pair of breathing tubes. A wye connector attached to an air supply which has a clip means which mates onto an annular groove on the tube means. No alignment or directionality is shown between the interfitting tubular members. Another connector means is shown in U.S. Pat. No. 3,409,859 wherein a lug is disposed within a cavity to help facilitate alignment of the connector halves. A problem with this connector means is that the means for insuring proper alignment or orientation of the connector halve is disposed within a cavity and is not readily viewable from the outside of the connector means. A further connector assembly is shown in U.S. Pat. No. 3,409,858 wherein an external clip on one side of the connector system facilitates locking and aligning thereof. Each element in the connector assembly however is not identical to the other halve. Each halve has to be made by itself and they are not interchangeable. A further connector arrangement is shown in U.S. Pat. No. 3,417,365. This connector means permits alignment of the connector assembly but it fails to permit a common element to be used in each connector halve.

It is an object of the present invention to provide a connector means which overcomes the disadvantages of the prior art.

It is a further object of the present invention to provide a connector assembly wherein each halve of the assembly may be used interchangeably with the other halve.

It is yet a further object of the present invention to provide a connector assembly for a plurality of fluid lines, which connector assembly is readily alignable, and impossible to misalign.

It is still yet a further object of the present invention to provide a connector assembly for connecting a plurality of fluid lines in a fast, sure and safe manner.

BRIEF SUMMARY OF THE INVENTION

The present invention comprises a manifold coupling or connection arrangement for joining a plurality of fluid carrying tubes with a corresponding plurality of fluid carrying tubes. The connection arrangement permits continuous, replaceable proper alignment between the respective tubes in the series. Each halve of the connector arrangement comprises a manifold halve having a bulkhead transversely disposed intermediately therein. Each manifold halve of the manifold coupling or connector assembly is identical to the other halve of connector assembly. A plurality of tubular members extend through the transverse bulkhead and provide fluid communication therethrough. The housing defines a first cavity on the larger side of the bulkhead and a second cavity on the smaller side of the bulkhead. The cavity is defined by a pair of sidewalls and a pair of end walls. One sidewall has a pair of primary keying members thereon and the other sidewall has three primary keying members thereon. Each primary keying member is parallel to the other keying members and run parallel to the longitudinal axis of the connector halve. Each end wall of the larger cavity has a peripheral opening and a further opening thereadjacent to receive a tip of an interlocking finger. Each sidewall has a periphery with a flange thereon to provide strength and resistance to bending within the sidewall. The larger cavity of one particular connector halve defines the female socket portion of the connector system.

The housing defining the smaller portion of another connector halve, which defines the male portion of the connector system, consists of a pair of sidewalls and a pair of end walls. Each sidewall has an arrangement of keyways thereon, one sidewall having three keyways parallel to one another and the other sidewall two keyways thereon, parallel to one another. The end wall of each of the smaller cavity portions has a finger extending longitudinally therealong from adjacent the transverse bulkhead. The distal end comprises the interlocking portion which is adapted to mate with the opening in the sidewalls of the female portion of the other housing. A flexible conduit may be arranged onto each of the tubular elements which extends from the transverse bulkhead to one halve of the connector elements from the female or larger portion thereof. The other halve of the connector assembly may have a conduit extending from each tubular member on the smaller or male side of the transverse bulkhead.

To effectuate the interconnection and fluid communication between the conduits connected to each of the respective manifold halves of the manifold connector assembly, the keyways on the outside of the housing on the male end of the first manifold are aligned with the primary keys of the housing on the female side of the second manifold and the two manifolds are pressed theretogether to make the manifold assembly. The primary keys mate with the proper keyways and insure proper alignment between the conduits. A second set of keys are arranged on the outside of the sidewalls on the male portion to further prevent 180° misalignment when the halves are inserted together. The flexible finger elements of the end walls of the first connector halve have their tab portions mate with the openings in the end walls of the second connector halve. Thus the articulated fingers permit the two manifold halves from being accidently withdrawn and separated. The ridge on the periphery of the female side of the second connector prevents yielding of the sidewalls thus preventing the jamming of the two halves together.

The outside wall surface of the larger housing may have indicia inscribed thereon to further insure that proper alignment will occur when the halves are mated to form an interconnection system.

BRIEF DESCRIPTION OF THE DRAWINGS

The object and advantages of the present invention will become more apparent when viewed in conjunction with the following drawings, in which:

FIG. 1 is a perspective representation of the two manifoldd halves of the manifold coupling assembly connected theretogether;

FIG. 2 is a side elevational view of the front side of one of the manifold halves;

FIG. 3 is an end view of one of the manifold halves;

DESCRIPTION OF THE PREFERRED EMBODIMENT

Figure 4:
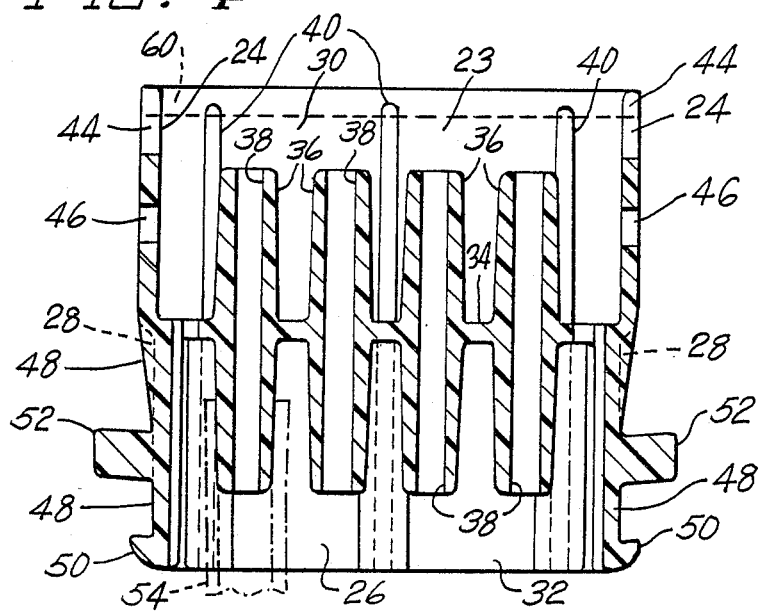
FIG. 4 is a view taken along the lines IV—IV of FIG. 3.

Referring now to the drawings in detail, and particularly to FIG. 1, there is shown a manifold connector assembly or manifold coupling assembly 10, comprising a manifold halve 12 acting as a male manifold here and a (second) manifold halve 14 acting as a female manifold here. A plurality of fluid conduits 16 and 18 are shown in fluid communication with their respective manifold 12 and 14. Each manifold 12 and 14 is identical with the other, so as to provide a greater economy of manufacture and design.

The manifold 12, shown as an example for both halves in FIGS. 2 and 3, comprises an enlarged upper housing 20 and a smaller lower housing 22. The upper housing 20 has a pair of sidewalls 23 and a pair of end walls 24. The lower housing 22 has a pair of sidewalls 26 and a pair of end walls 28. The upper housing 20 has an opening 30 of proper dimensions so as to permit the snug entry of the lower housing 22 of another manifold therewithin, or the receipt of plurality of conduits 16, as shown in FIG. 1.

Figure 5:
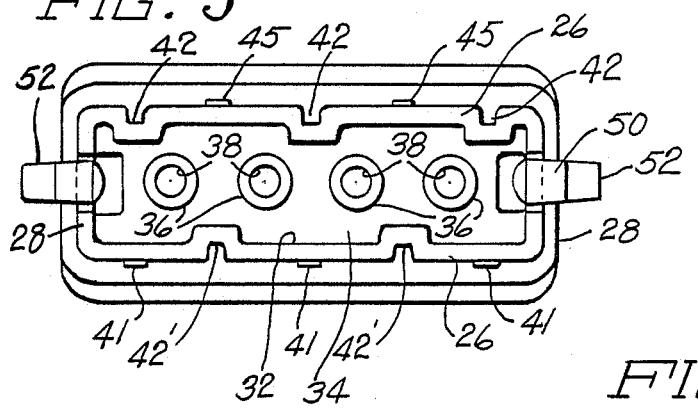
FIG. 5 is a view taken along the lines V—V of FIG. 3.
Figure 6:
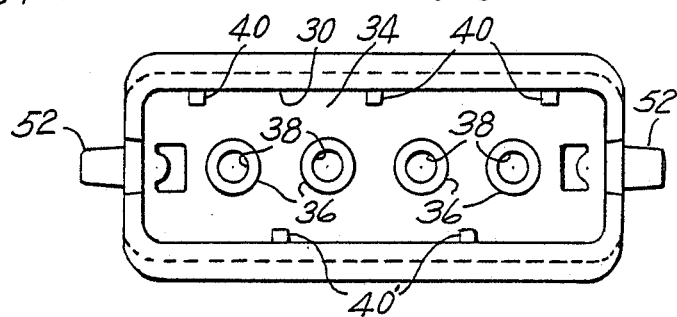
FIG. 6 is a view taken along the lines VI—VI of FIG. 3.

The lower housing 22 has an opening 32, capable of receiving a plurality of conduits 18 therewithin. The opening 30 in the upper housing 20 is separated from the opening 32 in the lower housing 22, by a bulkhead 34, as shown in FIGS. 4, 5 and 6. The bulkhead 34 has a plurality of tubing channels 36 disposed therethrough, so as to provide means for fluid communication between the two openings 30 and 32. Each tubing channel 36 has a bore 38 extending therethrough.

A particular number of primary keys 40 (three) are shown extending on the inside of one of the sidewalls 23 of the upper housing 20, as may be seen in FIGS. 4 and 6. A same number of keyways 42 are formed into the outside of one of the sidewalls 26 of the lower housing 22, as may be seen in FIG. 5. The other sidewall of the upper housing 20 and the other sidewall 26 of the lower housing 22 have a different number of keys 40' (two) thereon and keyways 42' therein, respectively, from the aforementioned sides.

An arrangement of three secondary keys 41 are shown disposed on the outside of the sidewall 26 on the lower (male portion) housing 22, as shown in FIG. 5. The three secondary keys 41 have pronounced square ends 43. The other side of the housing 22 has a pair of secondary keys 45 thereon. These secondary keys 41 and 45 provide additional interference with the keys 40 and 40' if the manifold halve 12 acting as a male were inserted the wrong way into the manifold halve 14. That is, the primary keys 40 and 40' would strike the secondary keys 41 and 45 to prevent the wrong connection of the manifold halves 12 and 14.

The end walls 24 on the upper housing 22 each have a notch 44 cut-out at its periphery, as shown in FIG. 3. A locking means, comprising an orifice 46, is disposed in each end wall 24, adjacent the notch 44. A locking finger 48 is resiliently connected to each end wall 24, as also shown in FIG. 3. A tab 50 on the distal end of each finger 48 is disposed thereon, so as to mate and lock with the orifice 46 in the end wall 24 of a mating manifold 14. A release button 52 is disposed at a mid-point of each finger 48, to permit the finger 48 to be manually pressed inwardly to disengage the tab 50 from its respective orifice 46, thus permitting the unlocking and separation of a pair of manifolds 12 and 14 from one another. The release button 52 of the male manifold 12 sits in the notch 44 of the female manifold 14 with which it is locked.

A tubing adapter 54, is shown in phantom on one of the tubing channels 36, in FIG. 5. Tubing adapters 54 are short pieces of tubing that mate with the channels 36, may be placed on each tubing channel 36 in the lower housing 22 on the manifold 12 which is to comprise the male portion of the manifold coupling 10, depending upon which function the manifold was taking, the male or the female. They could also be placed on the tubing channels 36 in the upper housing 20, which would comprise the female portion of the manifold coupling 10. The adapters 54 provide the securement between the particular channels of each halve 12 and 14 to insure snug communication therebetween.

When the manifold halves 12 and 14 are mated together, the key arrangement 40 in the (female) upper housing 20 will mate only one way with the keyways 40 disposed on the outer side of the (male) lower housing 22. A reinforcing lip 60 is disposed along the peripheral edge of the sidewalls 24. The lip 60 will prevent the sidewalls 24 from bending and otherwise allowing the lower housing 22 of the male portion of the coupling 10, to improperly mate with the upper housing 20 of the female portion of the coupling 10. Thus, any sequential fluid pressure operations would not be permitted to be reversed by an improper connection of the coupling device of the present invention.

An indicia or marking arrow "A" may be disposed on the sidewalls, as shown in FIGS. 1 and 2 to provide visual indicia of proper alignment between the manifold halves.

I claim:

1. A manifold coupling for the oriented interconnection of a plurality of fluid conduits, comprising:
   a pair of manifold halves, each halve including an upper housing and a lower housing;
   an arrangement of sidewalls and end walls defining each of said housings;

a bulkhead disposed between each of said housings, with a conduit means disposed through said bulkhead;

a locking arrangement disposed on the end walls, so as to lock each halve to the other, regardless of which is utilized as a receiving halve;

each of said housings having a keying arrangement to permit proper orientation only, of one halve when it is mated with the other halve;

a particular number of keys are disposed on one side of said sidewalls of said housing in the coupling, and a same particular number of keyways are disposed in the contiguous side of said sidewalls of the other housing in the coupling; and only said sidewalls having straight reinforcing means extending along their peripheral edges to prevent yielding thereof and improper interconnection therebetween.

2. A manifold coupling as recited in claim 1, wherein said reinforcing means extending along the peripheral edges comprises a reinforcing lip to prevent the sidewalls from bending.

* * * * *